United States Patent
Suri

(10) Patent No.: US 8,202,731 B2
(45) Date of Patent: Jun. 19, 2012

(54) HPTS-MONO AND BIS CYS-MA POLYMERIZABLE FLUORESCENT DYES FOR USE IN ANALYTE SENSORS

(75) Inventor: Jeff T. Suri, Rancho Santa Margarita, CA (US)

(73) Assignee: Glumetrics, Inc., Irvine, CA (US)

( * ) Notice: Subject to any disclaimer, the term of this patent is extended or adjusted under 35 U.S.C. 154(b) by 231 days.

(21) Appl. No.: 12/793,516

(22) Filed: Jun. 3, 2010

(65) Prior Publication Data

US 2010/0279424 A1 Nov. 4, 2010

Related U.S. Application Data

(63) Continuation-in-part of application No. 12/187,248, filed on Aug. 6, 2008, now Pat. No. 7,824,918.

(60) Provisional application No. 60/954,204, filed on Aug. 6, 2007.

(51) Int. Cl.
*G01N 33/50* (2006.01)
*C07C 309/00* (2006.01)

(52) U.S. Cl. .................. 436/95; 562/30; 562/7; 562/37; 562/39; 562/100

(58) Field of Classification Search .................... 436/95, 436/2; 562/30, 7, 37, 39, 100
See application file for complete search history.

(56) References Cited

U.S. PATENT DOCUMENTS 6,627,177 B2 * 9/2003 Singaram et al. ............. 424/9.6

FOREIGN PATENT DOCUMENTS

WO WO 2008141241 A1 * 11/2008

OTHER PUBLICATIONS

Suri, J.T. et al. 2003 "Continuous glucose sensing with a fluorescent thin-film hydrogel" *Angew Chem Int Ed* 42:5857-5859.
Cordes, D.B. et al. 2006 "Two-component optical sugar sensing using boronic acid-substituted viologens with anionic fluorescent dyes—Modulated quenching with viologens as a method for monosaccharide detection" in *Topics in Fluorescence Spectroscopy*, vol. 11, pp. 47-87.

* cited by examiner

*Primary Examiner* — Yelena G Gakh
*Assistant Examiner* — Christopher A Hixson
(74) *Attorney, Agent, or Firm* — Knobbe Martens Olson & Bear LLP

(57) ABSTRACT

Novel fluorescent dyes are disclosed for use in analyte detection. In particular, mono- and bis-substituted HPTS dyes and methods of making them are provided.

9 Claims, 9 Drawing Sheets

HPTS-MONO AND BIS CYS-MA POLYMERIZABLE FLUORESCENT DYES FOR USE IN ANALYTE SENSORS

RELATED APPLICATIONS

This application is a continuation in part application of U.S. application Ser. No. 12/187,248, filed Aug. 6, 2008, which claims the benefit of U.S. Provisional Application No. 60/954,204 filed Aug. 6, 2007, both of which are hereby incorporated by reference in their entireties.

FIELD OF THE INVENTION

Novel fluorescent dyes are disclosed for use in analyte detection.

DESCRIPTION OF THE RELATED ART

Investigators have used fluorescent techniques to measure polyhydroxyl compound (e.g., glucose) concentrations in body fluids. For example, Russell, disclosed the use of a boronic acid functionalized dye that binds to glucose and generates a signal dependent on glucose concentration (U.S. Pat. No. 5,512,246). James et al. used the same principle but combined a fluorescent dye, an amine quenching functionality, and a boronic acid in a single complex moiety, the fluorescence emission from which varies with the extent of glucose binding (U.S. Pat. No. 5,503,770). Glucose sensors comprising a fluorescent dye and a quencher comprising a single viologen moiety appended with boronic acids have been synthesized and investigated (e.g., Suri, J. et al. 2003 *Angew Chem Int Ed Engl* 42:5857-5859; Gamsey, S. et al. 2006 *Langmuir* 22:9067-9074; Thoniyot, P. et al. 2006 *Diabetes Technol Ther* 8:279-287; Cordes, D. B. et al. 2005 *Langmuir* 21:6540-6547; Cordes, D. B. et al. 2005 *Org Biomol Chem* 3:1708-1713; Cappuccio, E. E. et al. 2004 *J Fluoresc* 14:521-533; Gamsey, S. et al. 2007 *J Am Chem Soc* 129:1278-1286 and Cordes, D. B. et al. 2006 *Angew Chem Int Ed Engl* 45:3829-3832).

Fluorescent dyes, including 8-hydroxypyrene-1,3,6-trisulfonic acid (HPTS) and its derivatives, are known and have been used in analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; International Application No. PCT/US2003/030167; and co-pending U.S. patent application Ser. Nos. 10/456,895 and 11/296,898; each of which are incorporated by reference in their entireties. Although International Application No. PCT/US2003/030167 describes bis-substituted HPTS derivatives, they are structurally different from the bis-substituted HPTS compounds disclosed herein and the synthesis methods described are different from the methods disclosed herein.

SEGUE TO THE INVENTION

As part of an ongoing effort to synthesize analyte sensors, we have developed new mono- and bis-substituted HTPS fluorescent dyes. These dyes may be used in combination with analyte-binding moieties to achieve real-time measurement of analyte levels in vivo.

SUMMARY OF THE INVENTION

Mono-Substituted Dyes

N-substituted mono-sulfonamide derivatives of HPTS having the generic structure below are disclosed in the present invention:

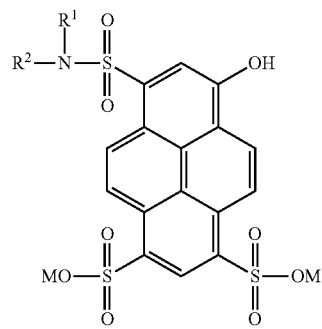

wherein $R^1$ and $R^2$ are independently selected from the group consisting of H, an anionic group and a reactive group, with the proviso that $R^1$ and $R^2$ collectively comprise at least one anionic group and at least one reactive group; and wherein M is a counterion.

In some embodiments, the anionic group is sulfonic acid.

In some embodiments, the reactive group is an ethylenically unsaturated polymerizable group selected from the group consisting of acryloyl, methacryloyl, acrylamide, methacrylamido, styryl, and the like.

In some embodiments, the reactive group comprises a coupling group selected from the group consisting of a carboxylic acid, aldehyde, alkyne, azide, activated ester, succinimide and nitrobenzoate, and wherein the coupling group is capable of binding the compound to a polymer or substrate.

In embodiments wherein one of $R^1$ and $R^2$ is H, the other group includes both an anionic group and a reactive group.

In some embodiments, $R^1$ and $R^2$ are bonded together in a cyclic structure.

1. Mono-CysMA

A mono-substituted fluorescent dye termed mono-CysMA having the structure below is disclosed in accordance with preferred embodiments of the present invention.

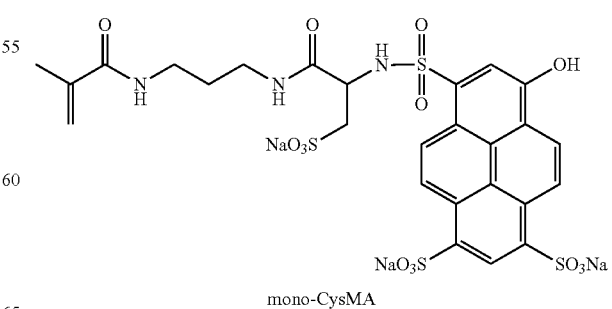

mono-CysMA

A method of making mono-CysMA is disclosed in accordance with another embodiment of the present invention. The method comprises the steps of:
(Scheme 1)
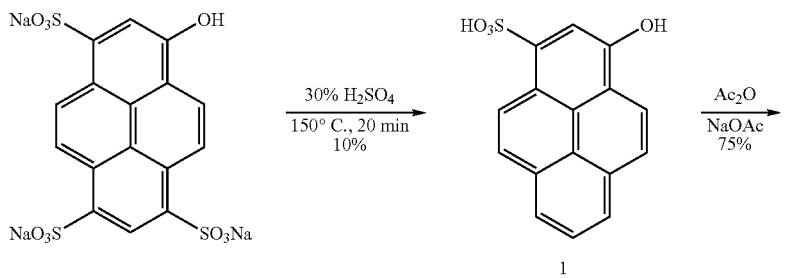
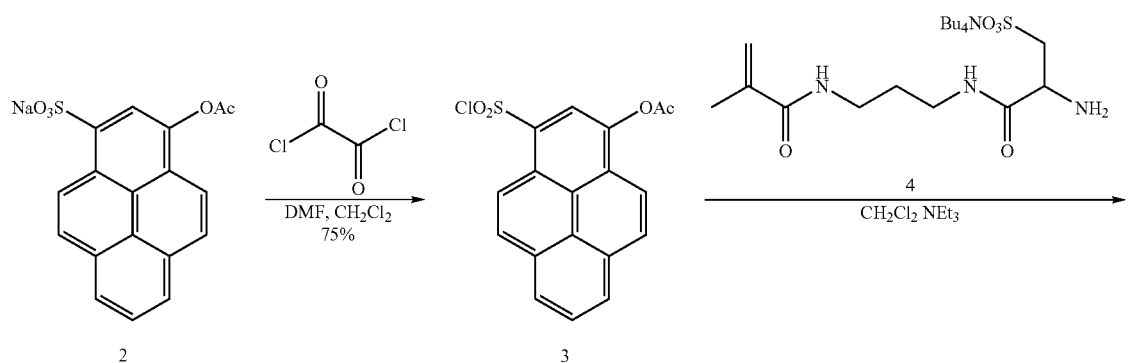
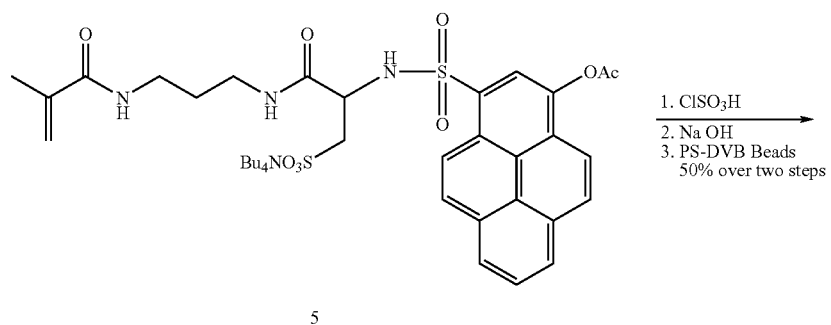
1. ClSO$_3$H
2. NaOH
3. PS-DVB Beads
   50% over two steps
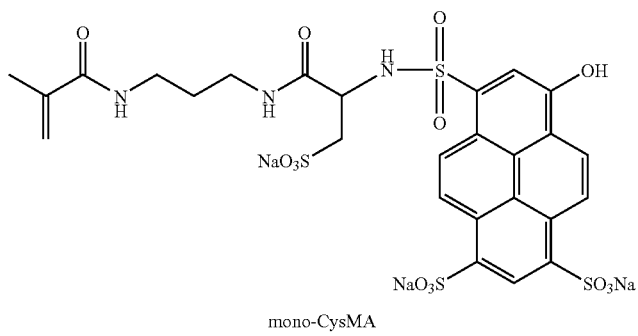
mono-CysMA

2. Mono-MA

Another mono-substituted fluorescent dye termed mono-MA having the structure below is disclosed in accordance with preferred embodiments of the present invention.

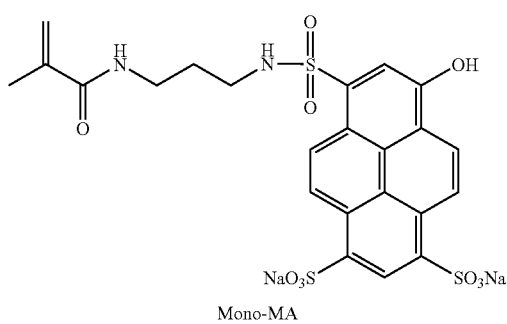

Mono-MA

A method of making mono-MA is disclosed in accordance with another embodiment of the present invention. The method comprises the steps of:

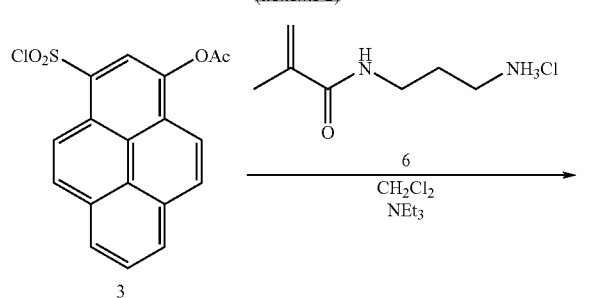

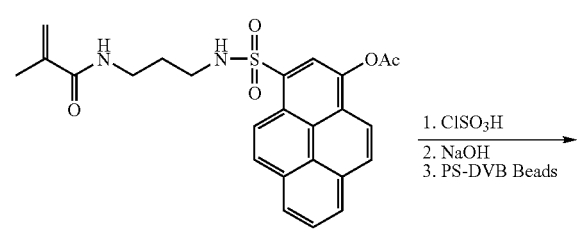

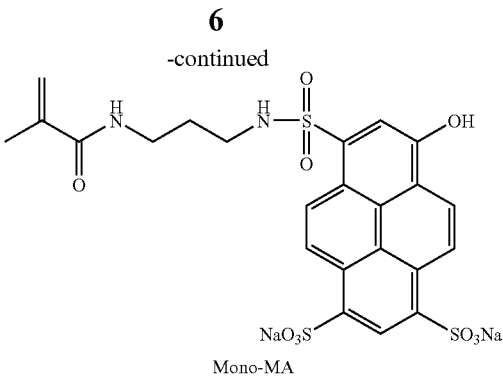

Mono-MA

Bis-Substituted Dyes

N-substituted bis-sulfonamide derivatives of HPTS having the generic structure below are disclosed:

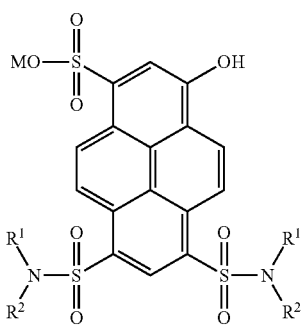

wherein $R^1$ and $R^2$ are independently selected from the group consisting of H, an anionic group and a reactive group, with the proviso that $R^1$ and $R^2$ collectively comprise at least one anionic group and at least one reactive group; and wherein M is a counterion.

In some embodiments, the anionic group is sulfonic acid.

In some embodiments, the reactive group is an ethylenically unsaturated polymerizable group selected from the group consisting of acryloyl, methacryloyl, acrylamide, methacrylamido, styryl, and the like.

In some embodiments, the reactive group comprises a coupling group selected from the group consisting of a carboxylic acid, aldehyde, alkyne, azide, activated ester, succinimide and nitrobenzoate, and wherein the coupling group is capable of binding the compound to a polymer or substrate.

In some embodiments, $R^1$ and $R^2$ are bonded together in a cyclic structure.

Bis-CysMA

A bis-substituted fluorescent dye termed bis-CysMA having the structure below is disclosed in accordance with preferred embodiments of the present invention.

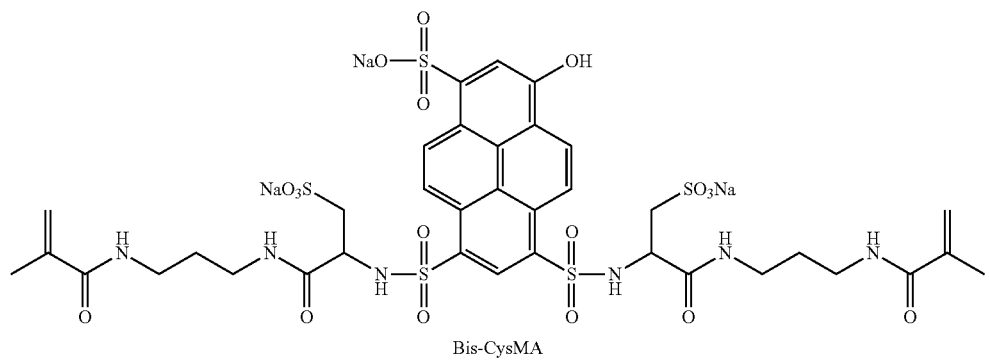
Bis-CysMA
A method of making bis-substituted dyes is disclosed in accordance with another embodiment of the present invention. The method comprises the steps of:
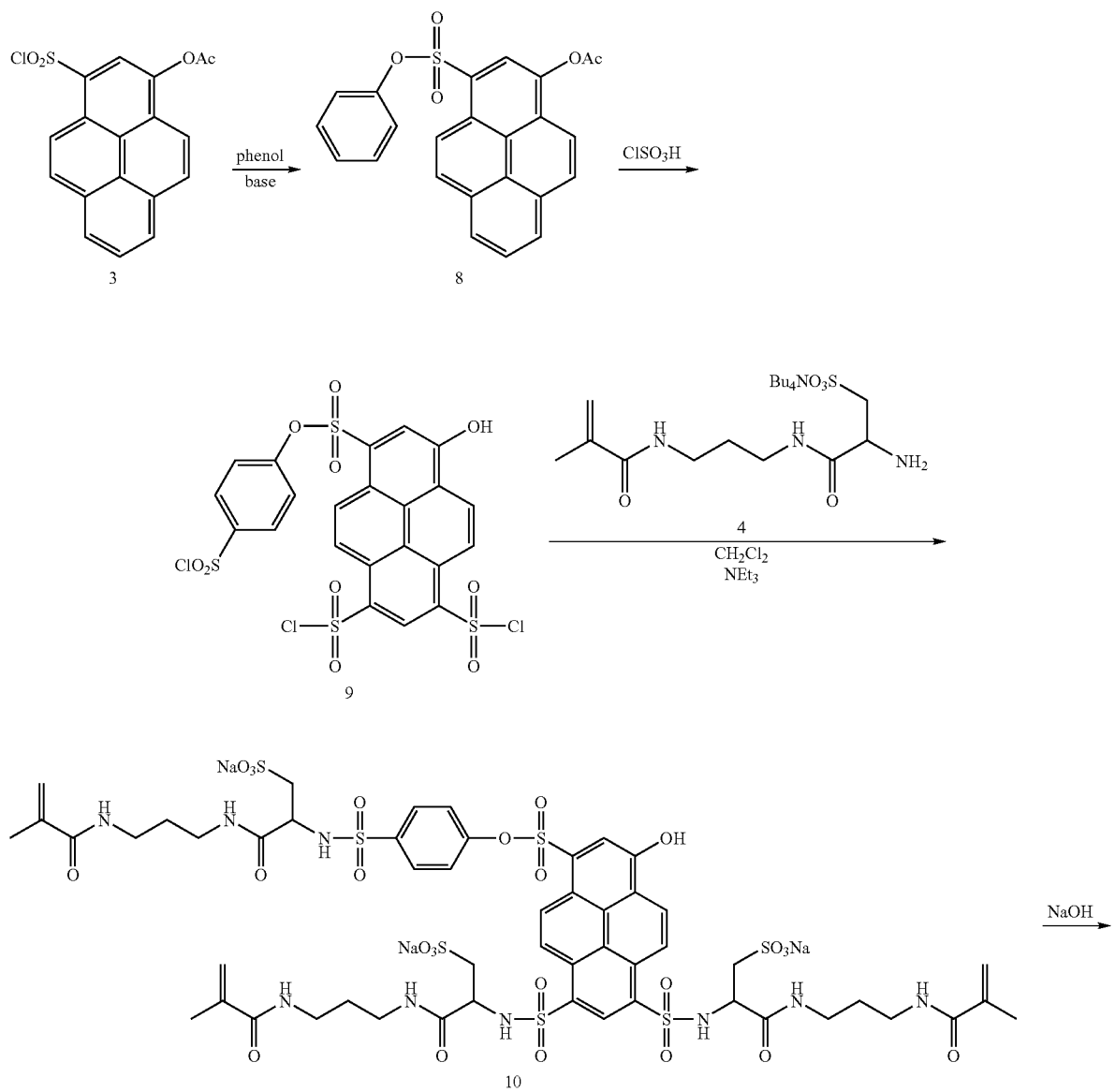

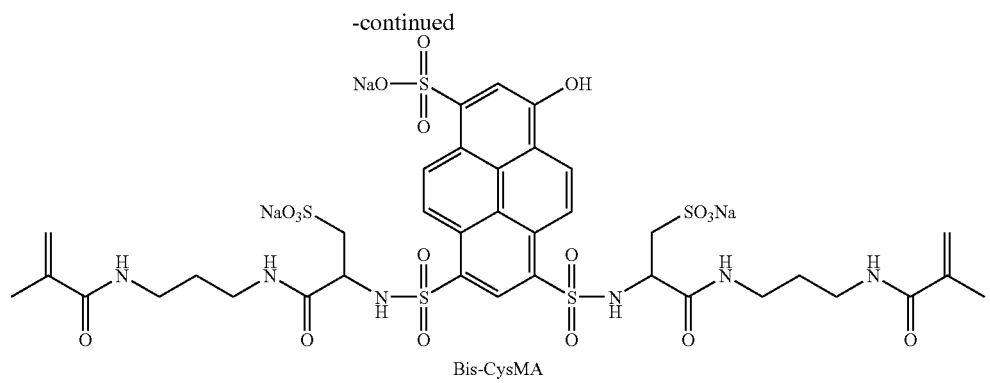
Bis-CysMA
Bis-MA
A bis-substituted fluorescent dye termed bis-MA having the structure below is disclosed in accordance with preferred embodiments of the present invention.
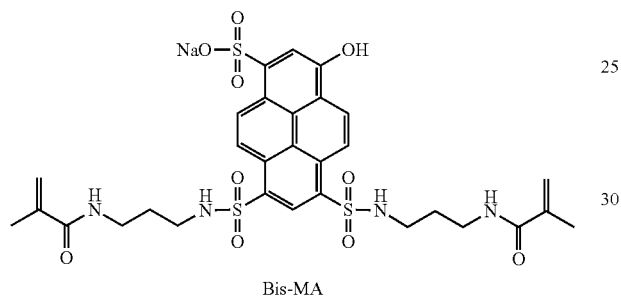
Bis-MA
A method of making bis-MA is disclosed in accordance with another embodiment of the present invention. The method comprises the steps of:
(Scheme 4)
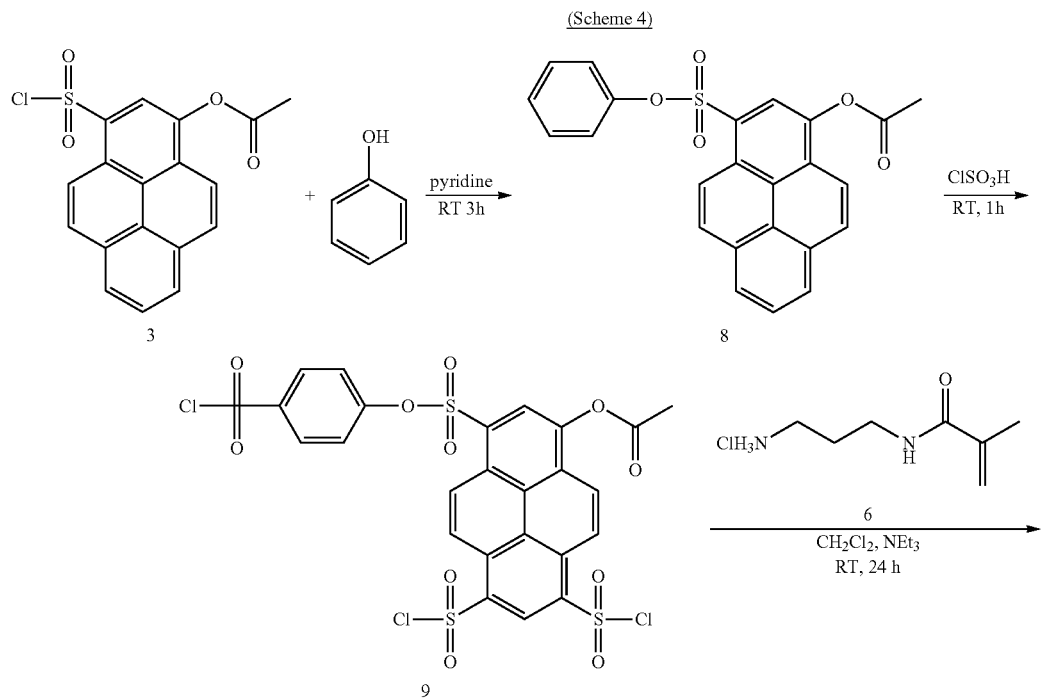

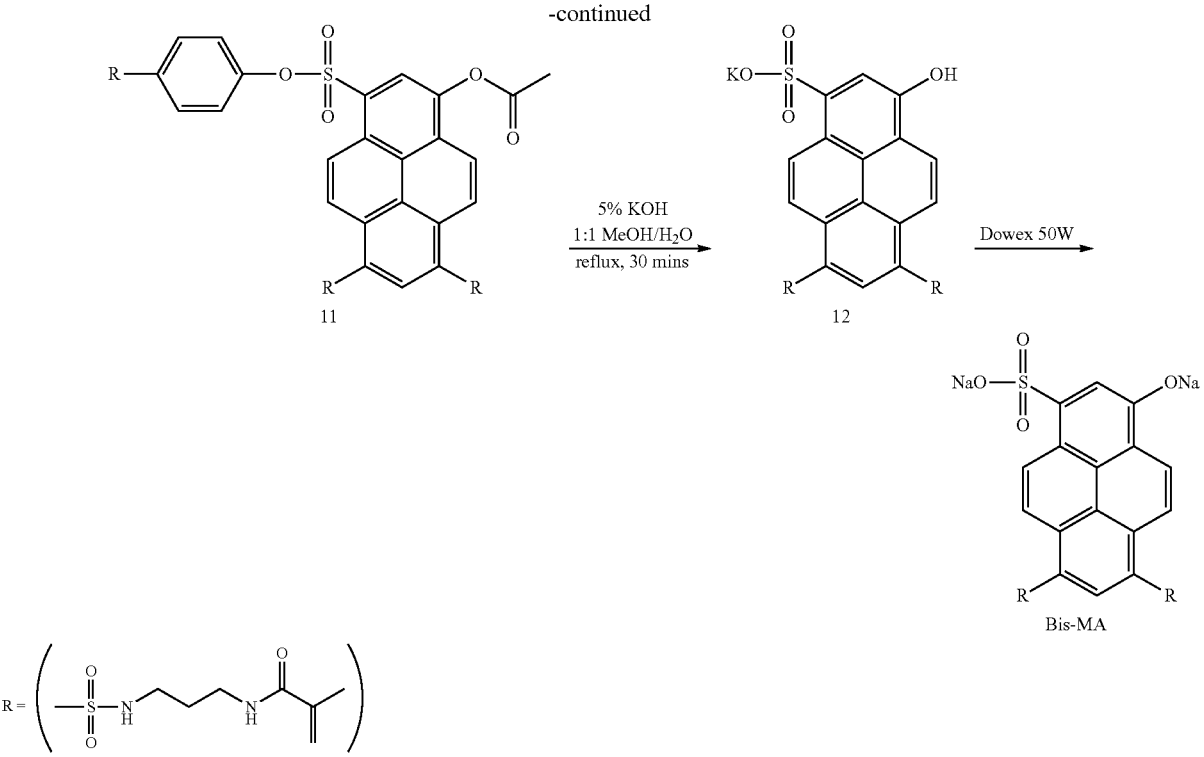

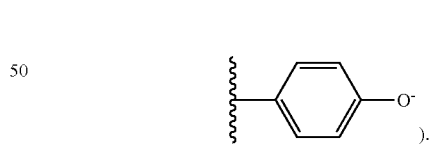

Glucose Sensors

A glucose sensor is disclosed in accordance with another embodiment of the present invention, comprising a mono- or bis-substituted dye described herein and a quencher comprising boronic acid such as boronic acid-substituted viologens, or pyridinium and quinolinium salts functionalized with boronic acids.

DETAILED DESCRIPTION OF THE PREFERRED EMBODIMENT

Dyes

Figure 1:
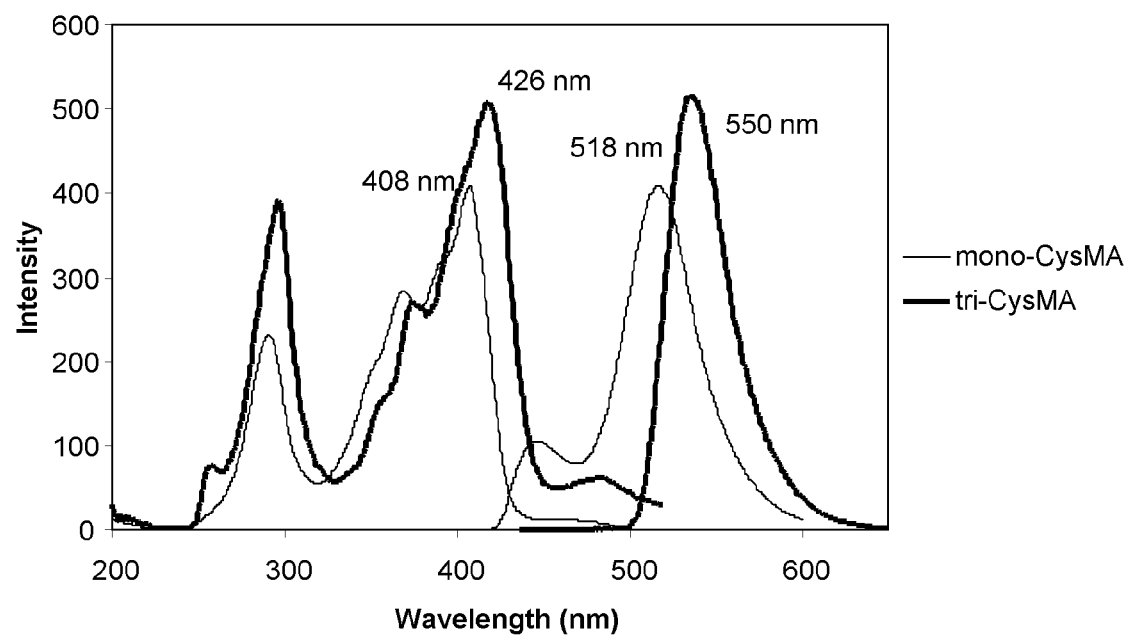
FIG. 1. Comparison of mono-CysMA with tri-CysMA in 40% DMAA at pH 5.

As used herein, the terms "fluorophore" or "fluorophore dye" or "dye" refer to a compound that, when exposed to light of appropriate wavelength, emits light, i.e., it fluoresces.

As used herein, a "coupling group" is a reactive functional group, capable of forming a covalent bond with a polymer, substrate matrix etc. especially with a preformed hydrogel. Such groups include, but are not limited to carboxylic acids, aldehydes, alkynes and azides, as well as activated esters, such as succinimides and nitrobenzoates, or any other mono-functional linker chemistry capable of covalently binding with polymer, substrate matrix etc. especially with a preformed hydrogel.

As used herein, an "anionic group" is any negatively charged group (e.g., $SO_3^-$, $HPO_3^-$, $CO_2^-$ and As used herein, a "counterion" is an ion that associates with an ion of opposite charge in the dye molecule. Non-limiting example counterions include ft, an alkali metal ion, $Li^+$, $Na^+$, $K^+$, $R^+$, $Cs^+$, $Fr^+$, an onium ion and $NR_4^+$, wherein R is selected from the group consisting of alkyl, alkylaryl and aromatic groups. One skilled in the art recognizes that the counterion does not influence the function of the dye when incorporated in a sensor. When the sensor is in a physiological fluid, the counterions equilibrate with the ions already present in the fluid.

The dyes of the invention are susceptible to quenching by electron acceptor molecules, such as viologens, they are resistant to photo-bleaching, and are stable to photo-oxidation, hydrolysis and biodegradation when used under conditions normally encountered in glucose sensing applications. In some embodiments, the dye is bound to a polymer through sulfonamide functional groups. The polymeric dyes may be water soluble, water insoluble, organic-solvent soluble or organic-solvent insoluble. For sensing to occur, the sensing moieties (analyte, dye and quencher) are in close physical proximity to allow interaction, i.e., mixed on a molecular level and in equilibrium with the species to be detected for quenching to occur.

Quenchers

As used herein, the term "quencher" refers to a compound that reduces the emission of a fluorophore when in its presence.

In some embodiments, a quencher moiety provides glucose recognition. Such moieties comprise an aromatic boronic acid. More specifically, the boronic acid is covalently bonded to a conjugated nitrogen-containing heterocyclic aromatic bis-onium structure (e.g., a viologen) in which the boronic acid reacts reversibly with glucose in aqueous, organic or combination media to form boronate esters. The extent of the reaction is related to glucose concentration in the medium.

Bis-onium salts are prepared from conjugated heterocyclic aromatic dinitrogen compounds. The conjugated heterocyclic aromatic dinitrogen are, e.g., dipyridlys, dipyridyl ethylenes, dipyridyl phenylenes, phenanthrolines, and diazafluorenes. It is understood that all isomers of said conjugated heterocyclic aromatic dinitrogen compounds in which both nitrogens can be substituted are useful in this invention.

In some embodiments, 3,3'-oBBV may be used as a quencher moiety. The structure of 3,3'-oBBV is:

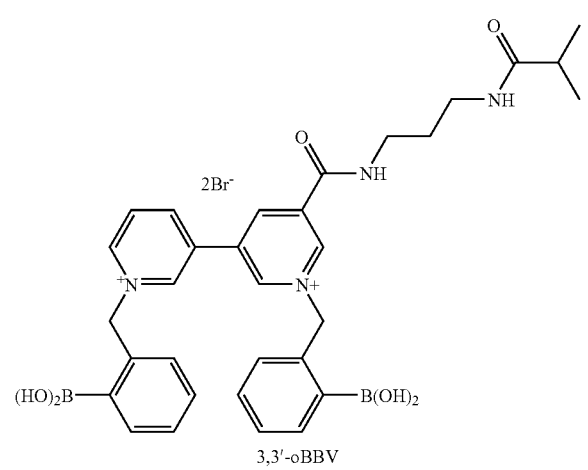

3,3'-oBBV

Mono-Substituted Dyes

N-substituted mono-sulfonamide derivatives of HPTS having the generic structure below are disclosed in the present invention:

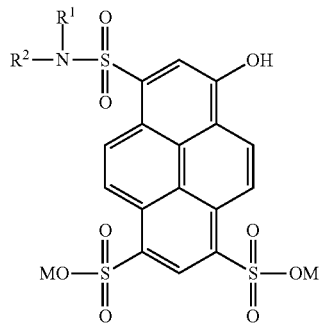

wherein M is a counterion and $R^1$ and $R^2$ are individually H— or an organic group or wherein $R^1$ and $R^2$ optionally comprising a reactive group and an anionic group, preferably a sulfonate ion, with the proviso that if one of $R^1$ and $R^2$ is H, the other is an organic group and if both $R^1$ and $R^2$ are organic groups at least one of $R^1$ and $R^2$ comprise a reactive group selected from a polymerizable group or a coupling group, preferably a polymerizable group. In some embodiments, $R^1$ and $R^2$ may be bonded together in a cyclic structure. Polymerizable groups are preferably ethylenically unsaturated groups including acryloyl, methacryloyl, acrylamide, methacrylamido, styryl, and the like. Coupling groups used to bond the dye to an existing polymer or substrate include, but are not limited to, carboxylic acids, aldehydes, alkynes and azides, as well as activated esters, such as succinimides and nitrobenzoates.

Dyes with only one polymerizable group are advantageous for making hydrogels and other sensing polymers because, in contrast to the polymerizable HPTS derivatives in the prior art, they do not act as crosslinkers. In addition, dye groups bonded to the polymer matrix at only one point are hypothesized to have greater mobility in the immobilized state thus allowing better interaction with the quencher. Interaction is further enhanced by the presence of acid groups that are fully ionized at physiological pH. Preferred dyes are mono-substituted derivatives of HPTS wherein one sulfonate group on the pyrene ring is converted to an N-substituted sulfonamide. The N—substituent comprises a linking group covalently bonded to an ethylenically unsaturated group, and optionally a sulfonic acid group, or salts thereof. Ethylenically unsaturated groups are preferably acryloyl, methacryloyl, acrylamido, methacrylamido, and styryl. Dyes with mono-substitution are also advantageous because the $pK_a$ of such dyes is optimized for physiological conditions, i.e., pH 7.4.

In some embodiments, N-substituted sulfonamide derivatives are formed by reaction of a sulfonyl chloride intermediate with a primary amine, $R^1$—$NH_2$. In other embodiments, N,N-bis-substituted sulfonamide derivatives are formed by reaction with a secondary amine, $R^1$—NH—$R^2$; optionally the R groups may be joined to form a cyclic secondary amine The following scheme includes examples of structures that encompass different types of mono-substituted dyes with secondary and aromatic amines:

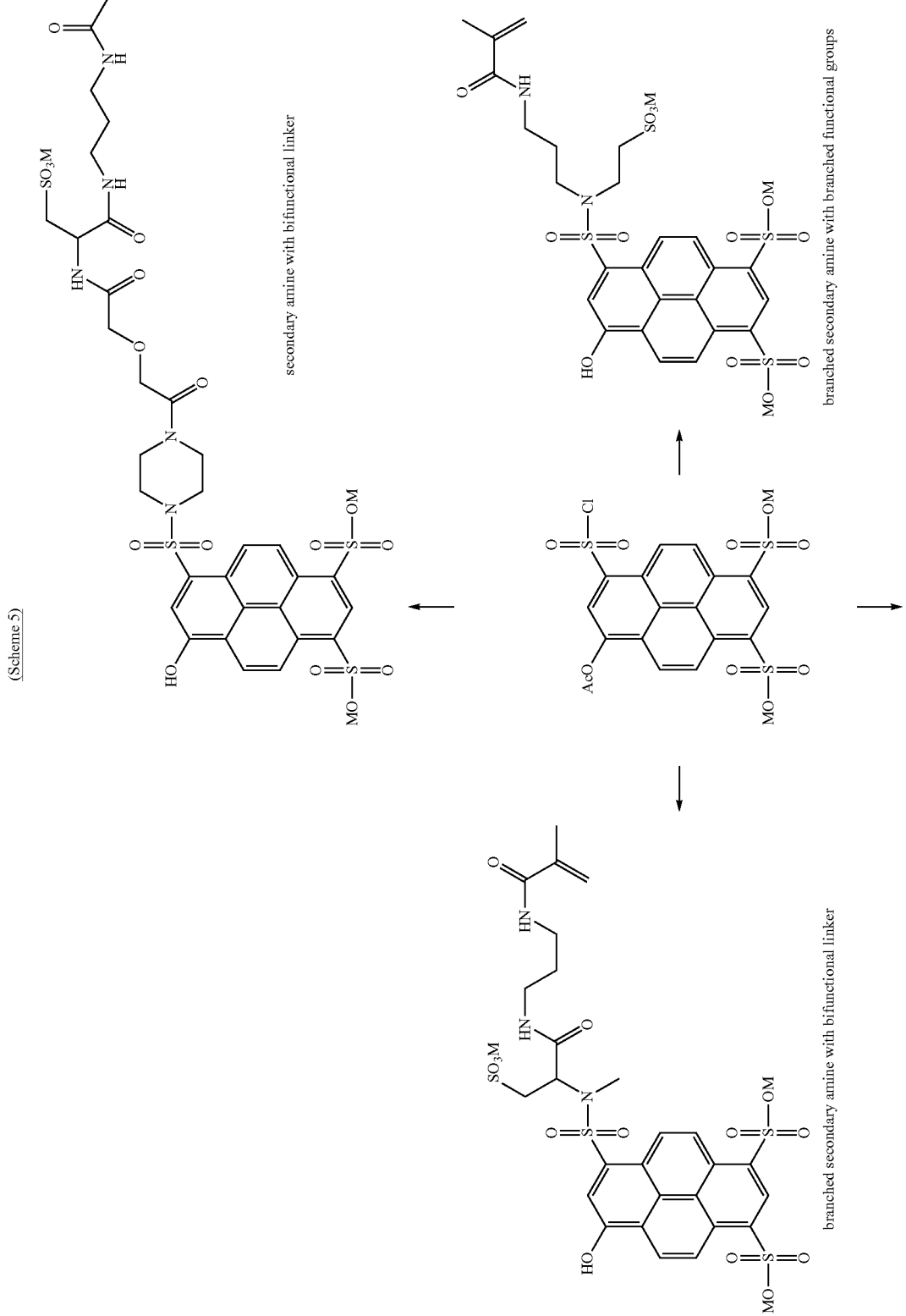

-continued
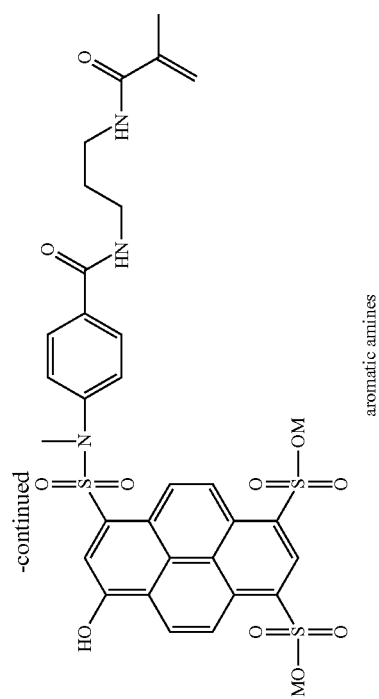
aromatic amines

Some HITS dye structures used herein include:

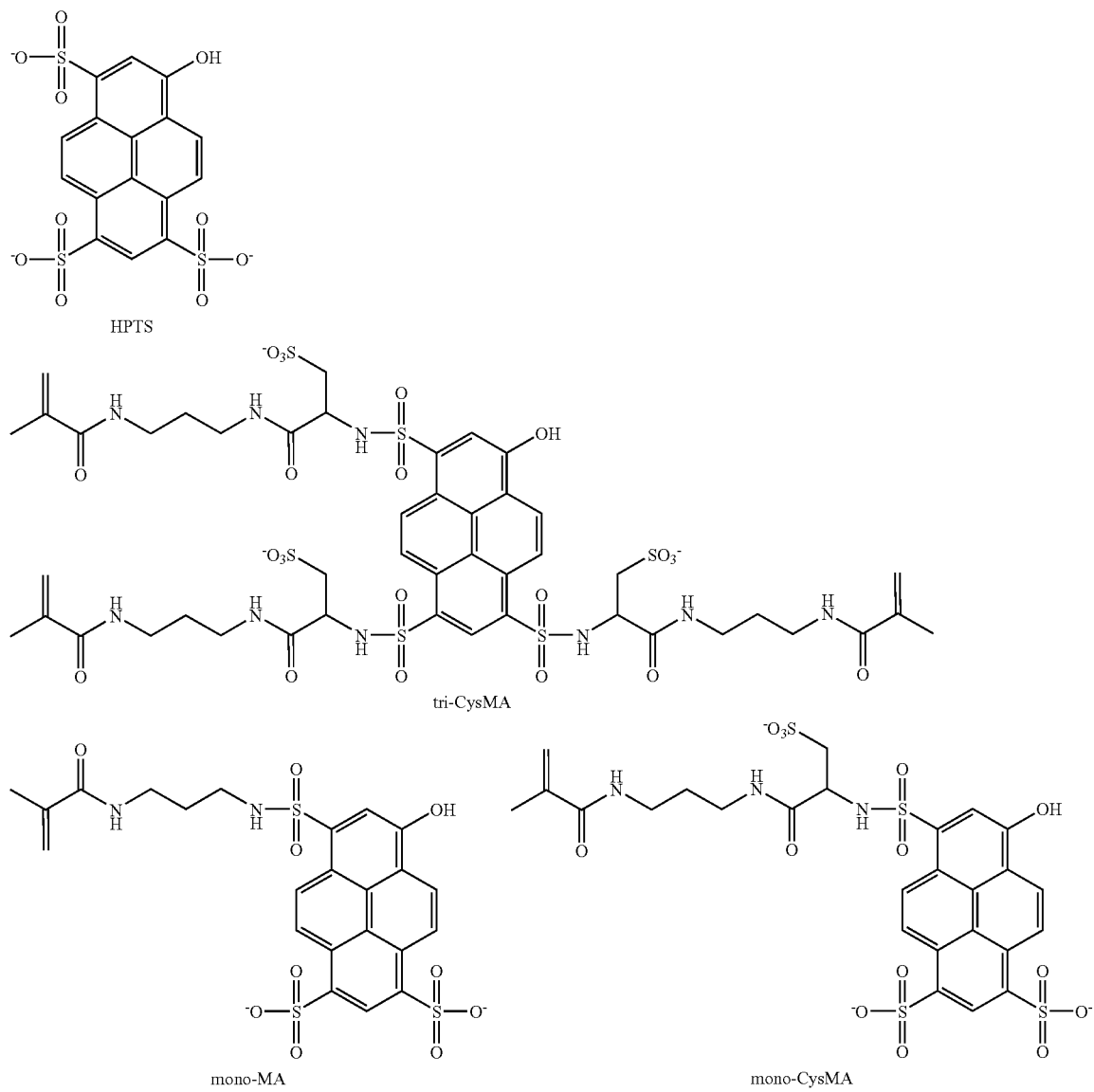

1. Mono-CysMA

The structure of mono-CysMA is:

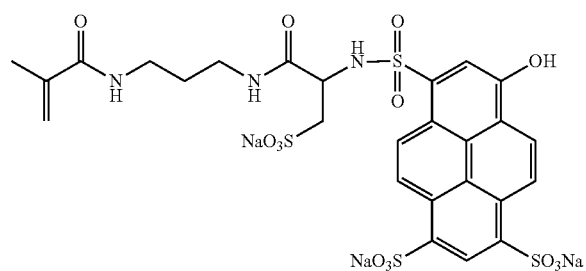

Of course, in some embodiments, substitutions other than Cys-MA on the HPTS core are consistent with aspects of the present invention, as long as the substitutions are negatively charged and have a polymerizable group. Either L or D stereoisomers of cysteic acid may be used. Likewise, in variations to mono-CysMA shown above, other counterions besides $Na^+$ may be used, e.g., $NBu_4^+$. In other variations, the sulfonic acid groups may be replaced with e.g., phosphoric, carboxylic, etc. functional groups.

The synthesis of mono-CysMA is given in Scheme 1. Reaction of HPTS with 30% sulfuric acid at 150° C. for 20 min gave sodium 3-hydroxypyrene-5-sulfonate 1 in 10% yield. Acetylation of 1 followed by chlorination of 2 gave intermediate 3. The polymerizable group was attached via the cysteic acid moiety in compound 4 and reacted with 3 to give compound 5. Chlorosulfonation of 5 was achieved without affecting the polymerizable group and after purification on polystyrene beads gave mono-CysMA in 50% yield over two steps. The dye was characterized by $^1H$ NMR, HPLC, and MS.

Referring to Scheme 6, a 50-mL round bottom flask equipped with a magnetic stirring bar was charged with HPTS (9.5 mmols, 5 g) and 30% $H_2SO_4$ (35 mL). The mixture was heated at 150° C. for 20 min and then allowed to cool at ambient temp for 10 min. The solution was poured into 100 g of crushed ice and diluted to 200 mL with water. The mixture was extracted with isopropyl acetate (200 mL×4) and concentrated in vacuo. The residue was mixed with silica gel (3 g) and crushed into a fine powder and dry loaded onto a Biotage 40 M cartridge. The residue was purified via gradient elution using 5% MeOH: (5% NEt$_3$:CH$_2$Cl$_2$) to 15% MeOH:(5% NEt$_3$:CH$_2$Cl$_2$) to give the triethylamine salt of 1 (0.281 g). The salt was treated with 1 M HCl and extracted with isopropyl acetate and the isopropyl acetate layer dried over MgSO$_4$ and concentrated in vacuo to give 1 as a brown/green foam. Synthesis of 1 was reported previously by E. Tietze and O. Bayer 1939 *Ann* 540:189-210. TLC (MeOH: CH$_2$Cl$_2$:NEt$_3$, 2:7:1) R$_f$=0.23. $^1$H NMR (500 MHz, CD$_3$OD) δ 7.94 (t, J=7.6 Hz, 1H), 7.97 (d, J=9.4 Hz, 1H), 8.02 (d, J=9.2 Hz, 1H), 8.11 (t, J=7.7 Hz, 2H), 8.25 (s, 1H), 8.39 (d, J=9.1 Hz, 1H), 8.98 (d, J=9.3 Hz, 1H).

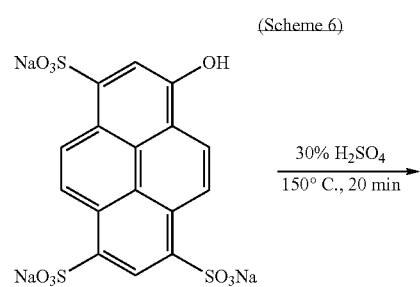

(Scheme 6)

Referring to Scheme 7, a 50-mL round bottom flask equipped with a magnetic stirring bar was charged with 1 (1.7 mmols, 0.5 g), acetic anhydride (30 mL), and sodium acetate (3.4 mmols, 0.279 g). The mixture was heated at 150° C. for 2 h and then allowed to cool to ambient temp. The solution was precipitated with ether:hexane (1:1, 50 mL) and the solid collected onto a fitted funnel and washed with ether. The solid was mixed with silica gel (3 g) and crushed into a fine powder and dry loaded onto a Biotage 40 M cartridge. The product was purified via gradient elution using 5% MeOH:CH$_2$Cl$_2$ to 15% MeOH: CH$_2$Cl$_2$ to give 2 (0.4636 g) as a cream-colored solid. TLC (20% MeOH: CH$_2$Cl$_2$) R$_f$=0.49.

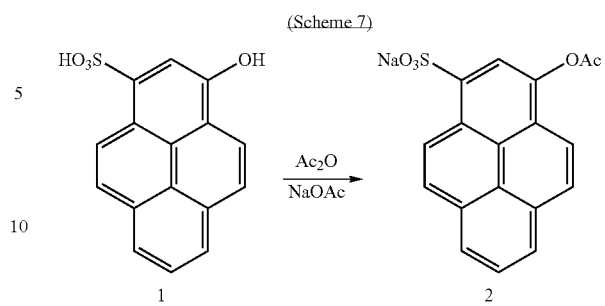

(Scheme 7)

Referring to Scheme 8, a 50-mL round bottom flask equipped with a magnetic stirring bar was charged with 2 (1.28 mmols, 0.463 g), CH$_2$Cl$_2$ (20 mL), and oxalyl chloride (3.84 mmols, 1.92 mL of 2.0 M solution in CH$_2$Cl$_2$). DMF (0.2 mL) was added dropwise and the mixture was refluxed for 27 h. The solution was cooled to room temp, mixed with 5 g of silica gel and filtered through a fritted funnel. The filtrate containing 3 was concentrated in vacuo to ca. 5 mL, and freshly prepared 4 (1.63 mmols, 0.872 g) was added along with NEt$_3$ (1.63 mmols, 0.227 mL). The mixture was stirred for 13.5 h at room temperature and the precipitate that formed was removed by filtration. The filtrate was concentrated in vacuo and loaded onto a Biotage 40M cartridge and was purified via gradient elution using 5% MeOH: (5% NEt$_3$: CHCl$_3$) to 30% MeOH: (5% NEt$_3$:CHCl$_3$). The desired fractions were combined and treated with 1 M HCl and extracted with EtOAc. The EtOAc layer was dried over MgSO$_4$ and concentrated in vacuo to give a yellow foam. The foam was treated with chlorosulfonic acid (5 mL) and the mixture was stirred for one hour at room temp. The solution was poured onto ice and made basic with 3M NaOH. The orange water layer was adsorbed onto polystyrene-divinylbenzene beads (250 g) and washed with water to remove any salts. The desired product was extracted from the beads using MeOH. The MeOH/water layer was concentrated in vacuo and then precipitated with acetone to give 0.1947 g of mono-CysMA. $^1$H NMR (500 MHz, D$_2$O) δ 0.80 (m, 2H), 2.12 (s, 3H), 3.09 (m, 4H), 3.24 (m, 2H), 4.26 (t, J=6.8 Hz, 1H), 5.15 (s, 1H), 5.21 (s, 1H), 8.19 (s, 1H), 8.54 (d, J=9.6 Hz, 1H), 8.91 (m, 3H), 9.14 (s, 1H); MS (MALDI-TOF) C$_{26}$H$_{27}$N$_3$O$_{14}$S$_4$, MH$^+$734.05.

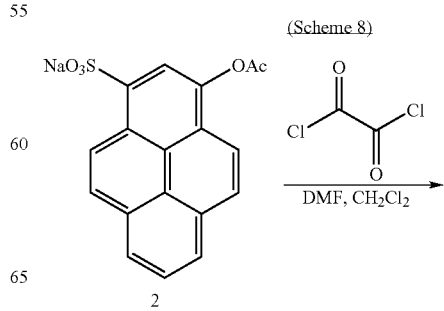

(Scheme 8)

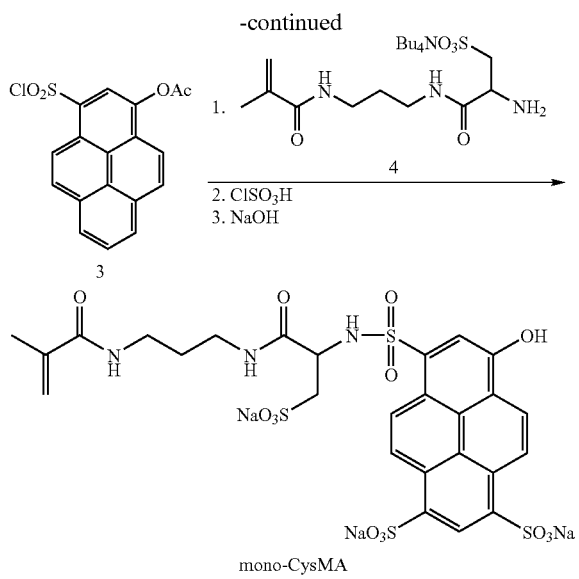

mono-CysMA

A hydrogel was prepared containing mono-CysMA, as described previously in U.S. patent application Ser. No. 11/671,880, to evaluate the fluorescence properties (excitation (ex), emission (em) and $pK_a$) of mono-CysMA. The excitation and emission spectra are given in FIG. 1 and are compared to tri-CysMA.

Figure 2:
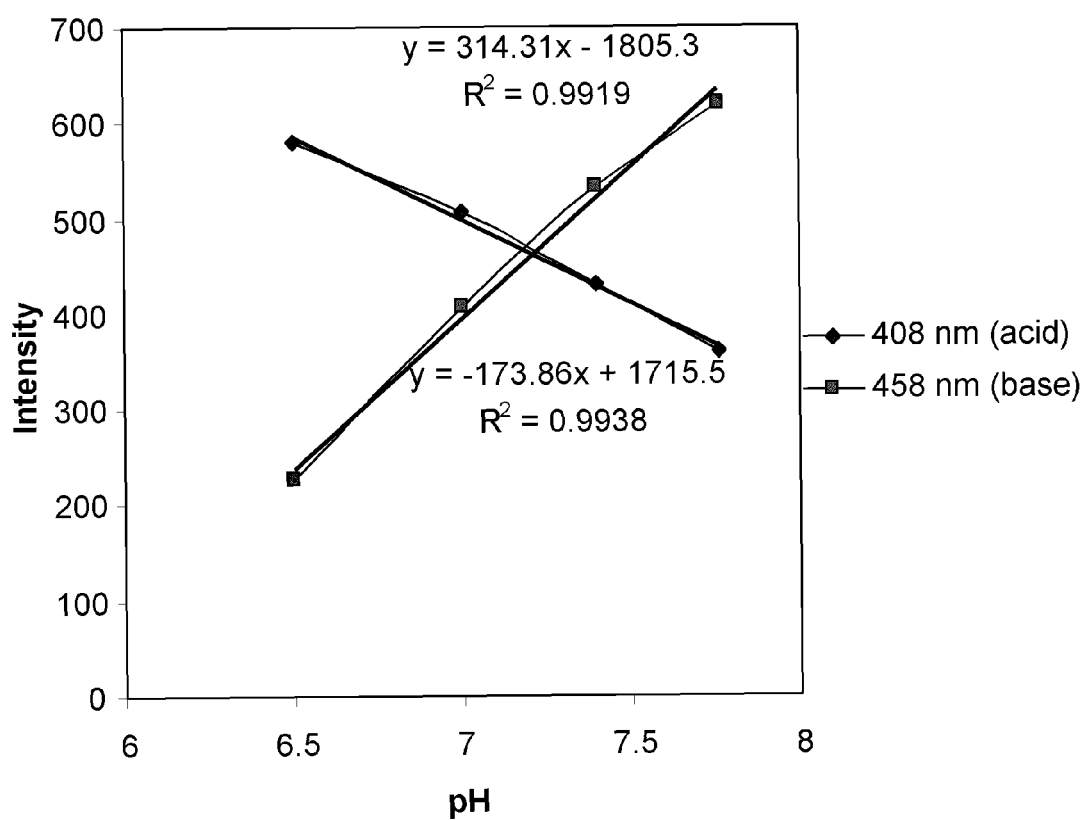
FIG. 2. pH profile of mono-CysMA.

A pH study was carried out with the gel. The data is summarized in FIG. 2. From this data the $pK_a$=7.2. Thus, mono-substitution allows for the incorporation of a polymerizable group and a sulfonate with minimal change of $pK_a$ relative to HPTS ($pk_a$=7.3).

Figure 3:
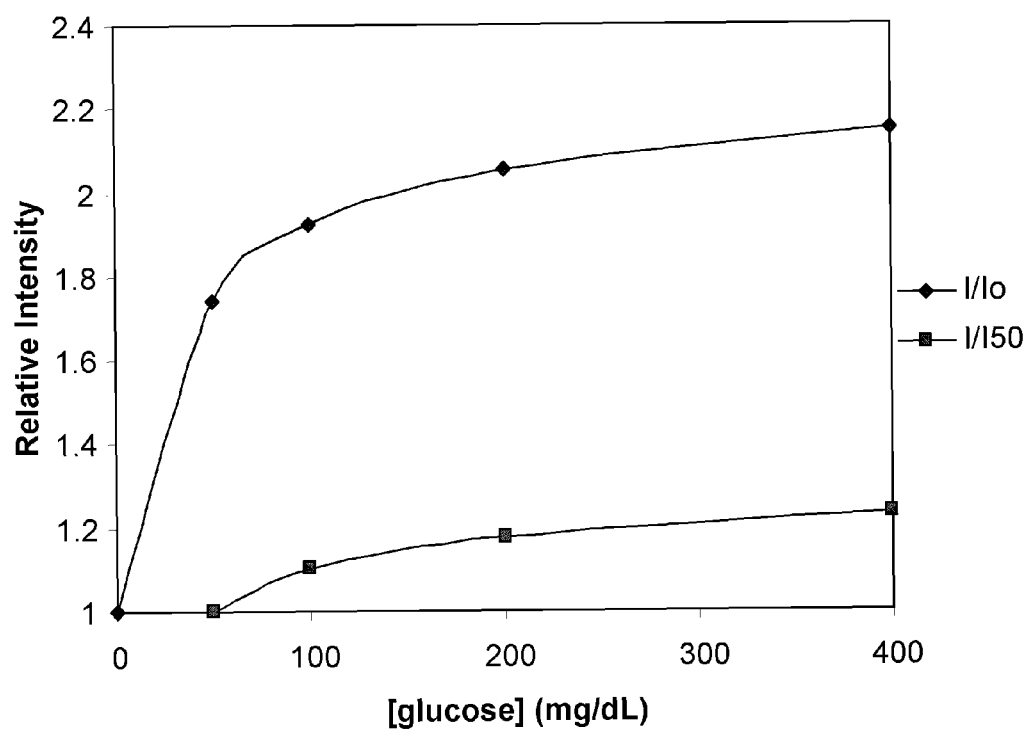
FIG. 3. Mono-CysMA response to glucose (mono-CysMA+3,3'-oBBV in 40% DMAA).

A 40% DMAA gel was prepared as previously described in U.S. patent application Ser. No. 11/671,880 (FIG. 3). Thus, the mono-CysMA functions as a pH sensitive dye and as a glucose sensitive dye (in the same way that tri-CysMA functions).

2. Mono-MA

The structure of mono-MA is:

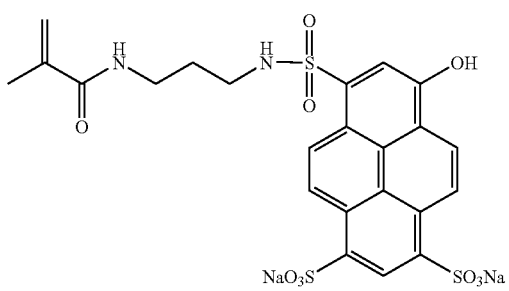

The synthesis of mono-MA is given in scheme 2. Reaction of 3 with aminopropyl methacrylamide gives pyrene 7. Chlorosulfonation of 7 gives the desired product Mono-MA. This dye is unique in that it contains only two negative charges. Thus, one dye molecule can associate with one quencher to give a charge-balanced 1:1 complex Referring to Scheme 9, mono-MA was made according to the following methods. A 50-mL round bottom flask equipped with a magnetic stirring bar was charged with 2 (0.591 mmols, 0.214 g), $CH_2Cl_2$ (10 mL), and oxalyl chloride (1.8 mmols, 0.9 mL of 2.0 M solution in $CH_2Cl_2$). DMF (0.1 mL) was added dropwise and the mixture was refluxed for 27 h. The solution was cooled to room temp, mixed with 5 g of silica gel and filtered through a fritted funnel. The filtrate containing 3 was concentrated in vacuo to ca. 5 mL, and 6 (0.65 mmols, 0.116 g) was added along with $NEt_3$ (0.7 mmols, 0.097 mL). The mixture was stirred for 20 h at room temperature and the precipitate that formed was removed by filtration. The filtrate was concentrated in vacuo and loaded onto a Biotage 40M cartridge and was purified via gradient elution using 5% MeOH: $CH_2Cl_2$ to 15% MeOH:$CH_2Cl_2$ to give a yellow solid (46 mg). The solid was treated with chlorosulfonic acid (1 mL) and the mixture was stirred for one hour at room temp. The solution was poured onto ice and made basic with 3M NaOH. The orange water layer was adsorbed onto polystyrene-divinylbenzene beads (50 g) and washed with water to remove any salts. The desired product was extracted from the beads using MeOH. The MeOH/water layer was concentrated in vacuo and then precipitated with acetone to give 8 mg of mono-MA.

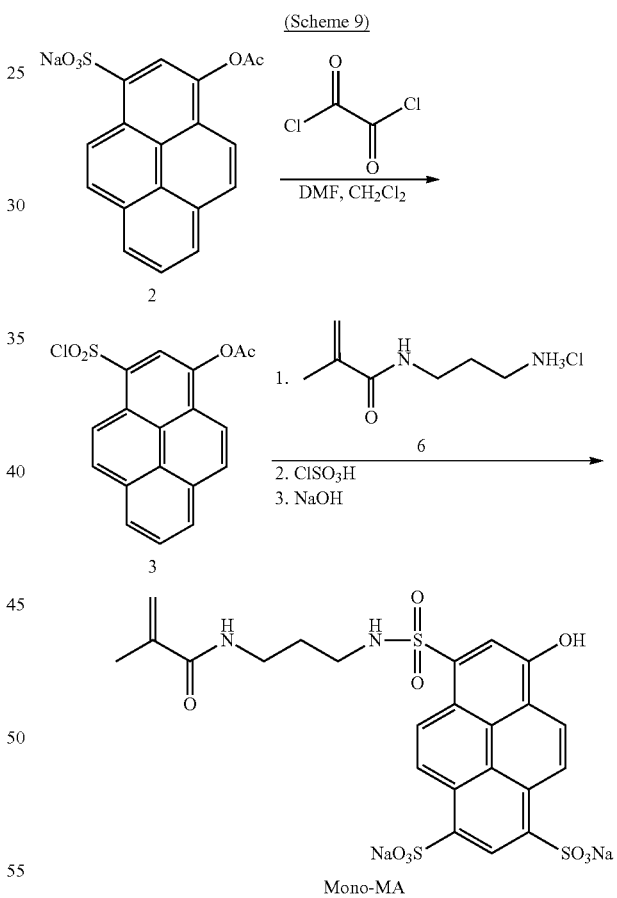

Figure 4:
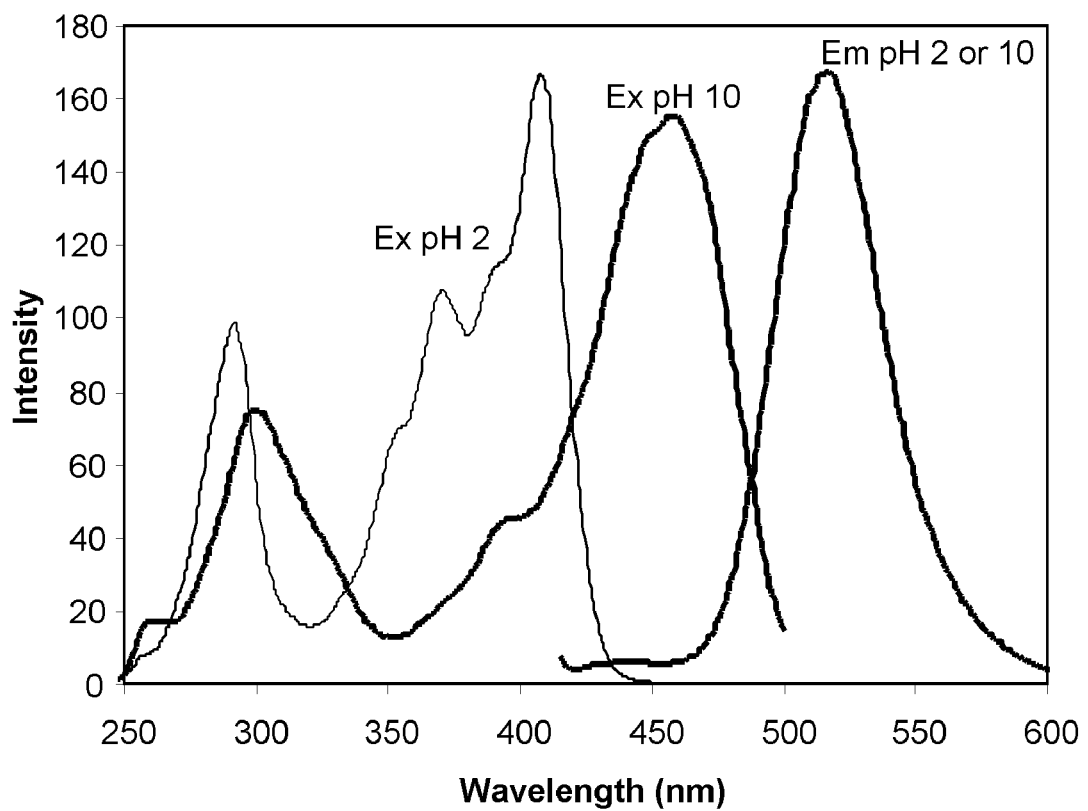
FIG. 4. Fluorescence spectra of mono-MA at different pH.
Figure 5:
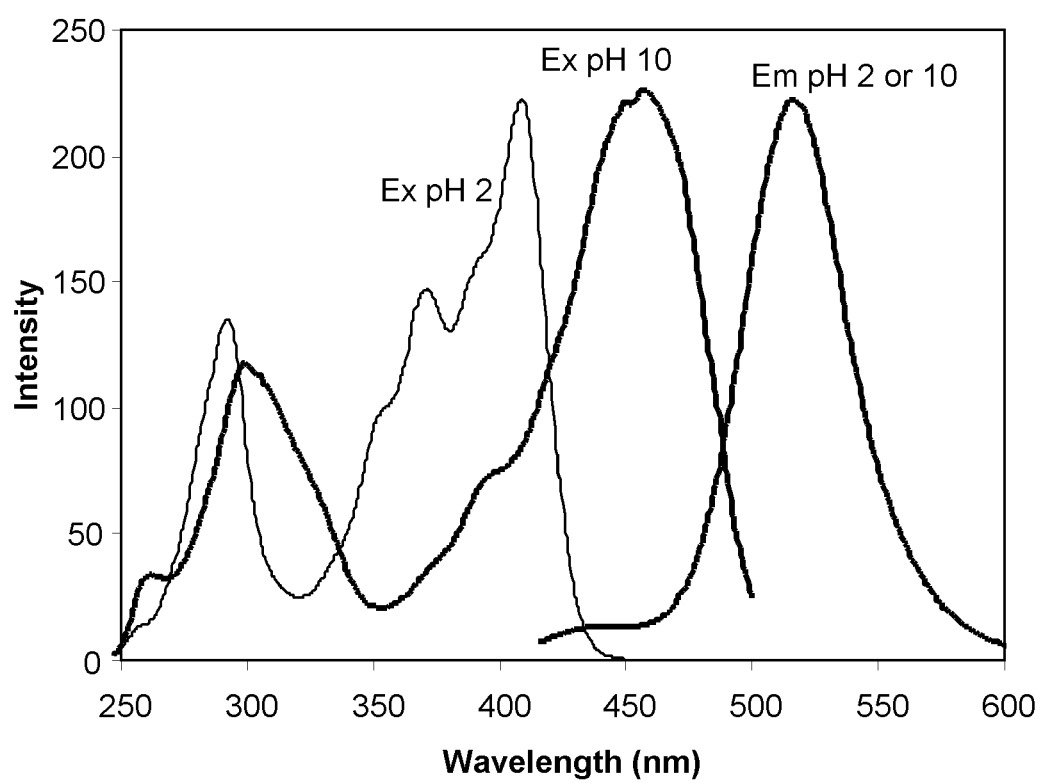
FIG. 5. Fluorescence spectra of mono-CysMA at different pH.
Figure 6:
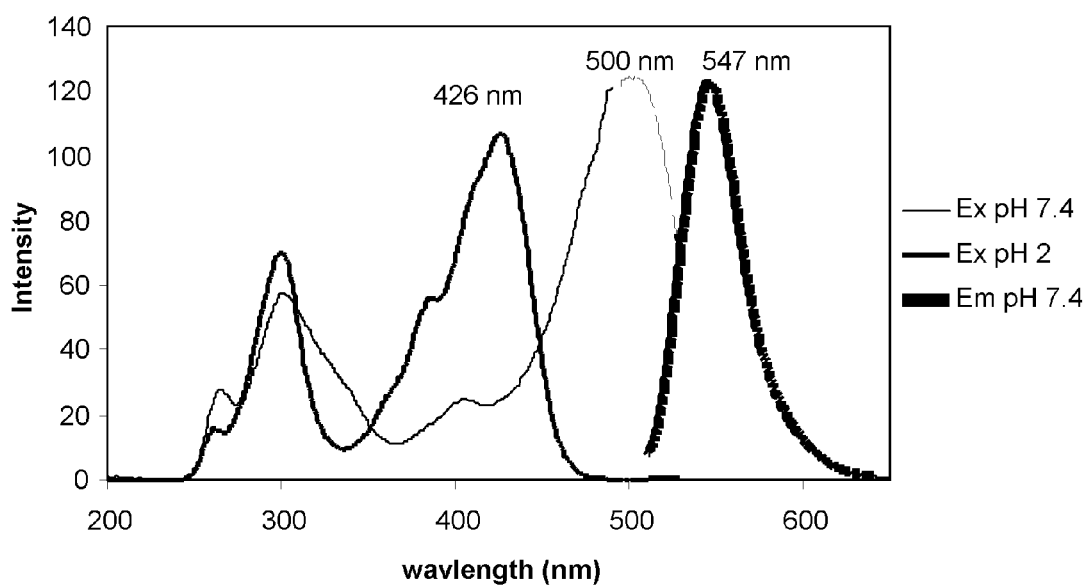
FIG. 6. Fluorescence spectra of tri-CysMA at different pH.

The quantum yield of Mono-MA was compared to other HPTS derivatives. A summary of the emission/absorbance (Em/Abs) ratios for HPTS, mono-MA, mono-CysMA and tri-CysMA are given in Table 1. We refer to this as the apparent quantum yield since the actual numbers are arbitrary but can be used for comparison. FIG. 4, FIG. 5 and FIG. 6 give the fluorescence excitation and emission spectra of mono-MA, mono-CysMA and tri-CysMA in a DMAA film, respectively at different pHs.

TABLE 1

Comparison of Dyes at $1 \times 10^{-5}$ M in pH 7.4 PBS

| Dye | Absorbance | Intensity at max | Ratio ("Quantum Yield") |
|---|---|---|---|
| HPTS | 0.15654 | 553 | 3533 |
| Mono-MA | 0.09003 | 258 | 2870 |
| Mono-CysMA | 0.15741 | 335 | 2128 |
| Tri-CysMA | 0.26113 | 351 | 1344 |

Figure 7:
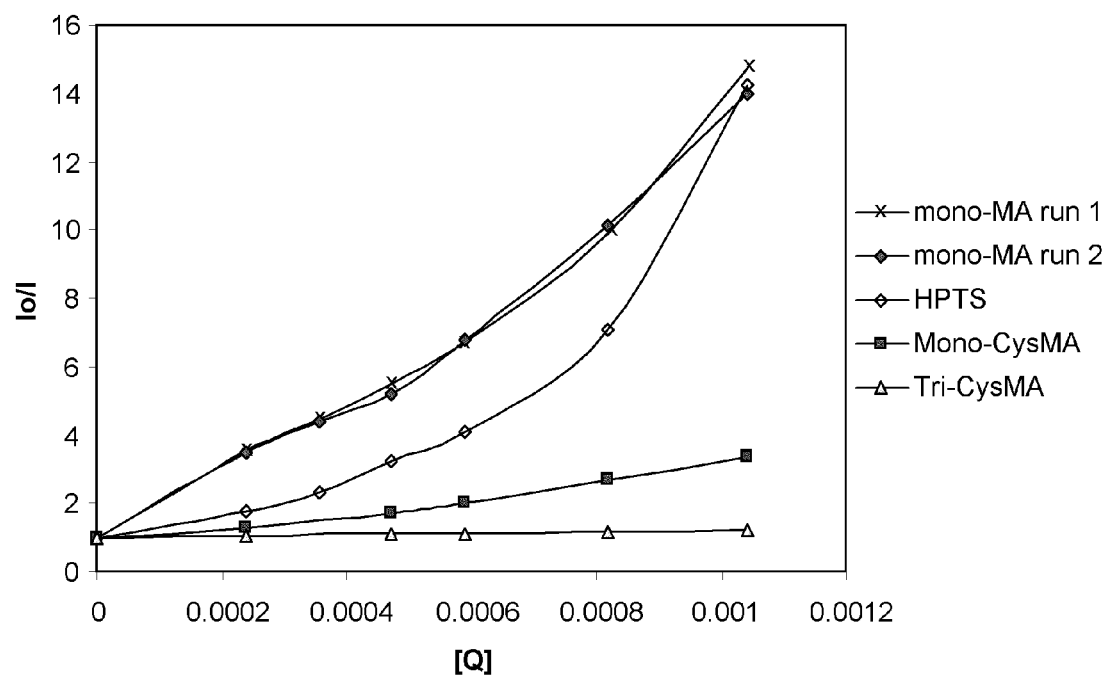
FIG. 7. Stern-Volmer comparison of HPTS dyes with 3,3'-oBBV.

The Stern-Volmer curves for all the dyes are summarized in FIG. 7. The mono-MA is quenched most efficiently relative to the other dyes. This appears to be a result of the charge-charge matching between the dye and the quencher; i.e., the dye has two negative charges and the quencher has two negative charges.

The three polymerizable dyes were immobilized using 40% DMAA and their $pK_a$ determined via a pH study. The results are summarized in Table 2.

TABLE 2

Determination of Dye pKa Values

| Dye | pKa |
|---|---|
| HPTS | 7.3 |
| Mono-MA | 6.7 |
| Mono-CysMA | 7.2 |
| Tri-CysMA | 6.2 |

Relative to HPTS, the mono-substituted dyes have lower $pK_a$s. Without wishing to be bound by any particular theory, the effective $pK_a$ of each dye appears to be the result of two structural modifications relative to HPTS: sulfonamide substitution on the pyrene core and anionic substitution on the linker. Dyes that are mono-substituted are advantageous because their $pK_a$s render them more sensitive to pH changes in the physiological range.

Figure 8:
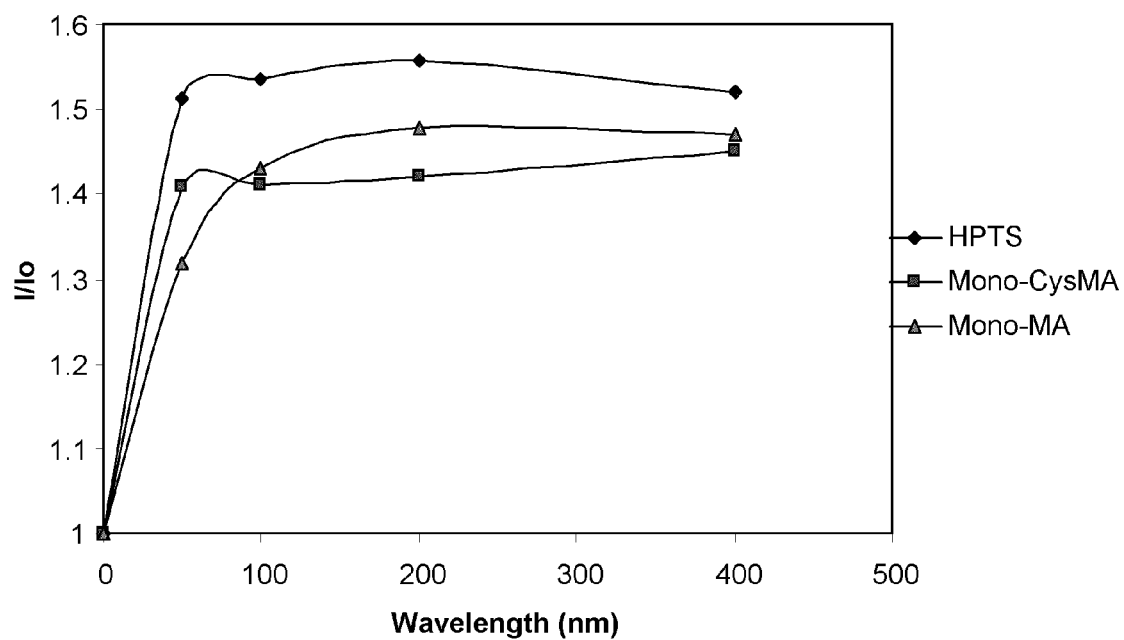
FIG. 8. Comparison of glucose response with different dyes and 3,3'-oBBV.

The dyes were tested in solution for glucose response in pH 7.4 PBS with 3,3'-oBBV (FIG. 8). The dyes were also immobilized in 40% DMAA gels using the recipe described previously and a glucose response experiment was carried out (FIG. 3).

Bis-Substituted Dyes

N-substituted bis-sulfonamide derivatives of HPTS having the generic structure below are disclosed:

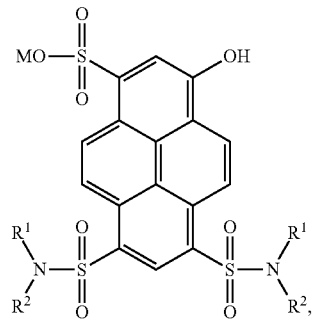

wherein M is a counterion and $R^1$ and $R^2$ are individually H— or an organic group, or wherein $R^1$ and $R^2$ optionally comprise a reactive group and an anionic group, preferably a sulfonate ion with the proviso that if one of $R^1$ and $R^2$ is H, the other is an organic group and if both $R^1$ and $R^2$ are organic groups at least one of $R^1$ and $R^2$ comprise a reactive group selected from a polymerizable group or a coupling group, preferably a polymerizable group. In some embodiments, $R^1$ and $R^2$ may be bonded together in a cyclic structure. Polymerizable groups are preferably ethylenically unsaturated groups including acryloyl, methacryloyl, acrylamide, methacrylamido, styryl, and the like. Coupling groups used to bond the dye to an existing polymer or substrate include, but are not limited to, carboxylic acids, aldehydes, alkynes and azides, as well as activated esters, such as succinimides and nitrobenzoates.

Bis-substituted dyes serve as crosslinkers. They also may have a more optimal $pK_a$, in comparison to tri-substituted dyes, that renders them more sensitive to pH changes in the physiological range. In addition, it is possible to have multiple functionalities attached to the dye (e.g., one sulfonamide may contain a polymerizable group while the other may contain an anionic group such as a sulfonic acid.

The following scheme includes examples of structures that encompass different types of bis-substituted dyes with secondary and aromatic amines:

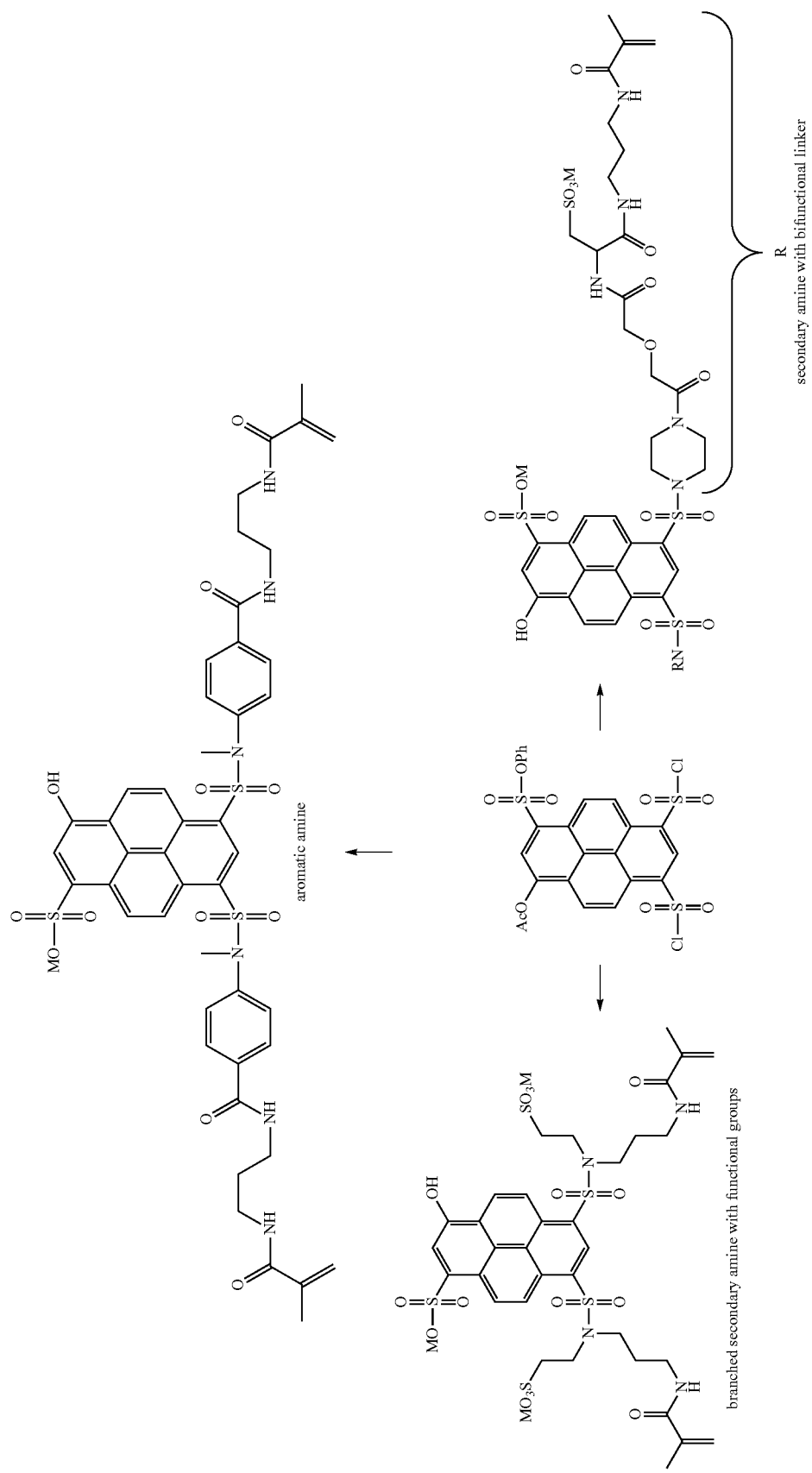

-continued
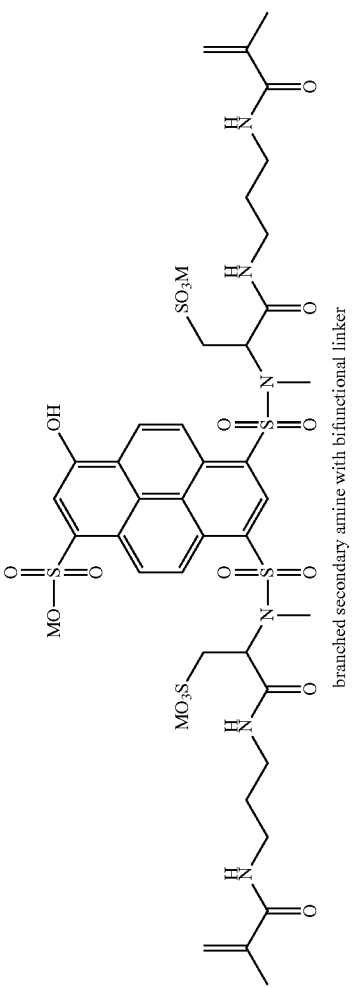

Bis-CysMA

A bis-substituted fluorescent dye termed bis-CysMA having the structure below is disclosed in accordance with preferred embodiments of the present invention.

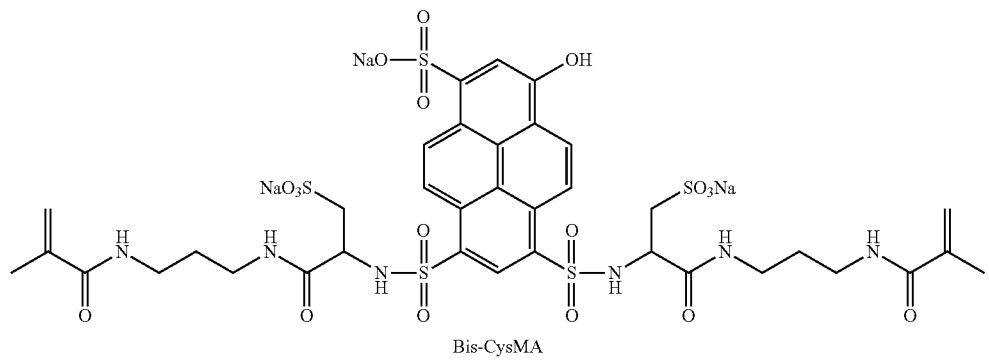

Bis-CysMA

A method of making bis-cysMA is disclosed in accordance with another embodiment of the present invention (Scheme 3).

Bis-MA

The synthesis of bis-MA is given in Scheme 4. Compound 3 is reacted with phenol in the presence of pyridine to obtain the sulfonate ester 8. Chlorosulfonation of 8 is carried out to give the bis-sulfonyl chloride 9. Reaction of 9 with 4 gives 10, which upon deprotection with base, gives Bis-MA. Below are the details regarding the sequence of reactions to synthesize Bis-MA.

Referring to Scheme 11, a 20-mL scintillation vial equipped with a magnetic stir bar was charged with 3 (0.84 mmols, 300 mg), pyridine (2 mL), and phenol (0.92 mmols, 86.6 mg). The cloudy yellow-brown solution was stirred at room temperature for 3 h and quenched with 15 mL 3M HCl to give a creamy white precipitate. The suspension was extracted with ethyl acetate and dried over MgSO$_4$ and concentrated to give 0.4 g of crude yellow solid. The solid was re-dissolved in ethyl acetate and combined with 2 g silica gel and dry loaded onto a Biotage Si 25+M cartridge. The product was eluted with ethyl acetate in hexane. The collected fractions were concentrated to give 8 as a bright yellow crystalline solid (0.15 mmols, 59 mg, 18%).

-continued

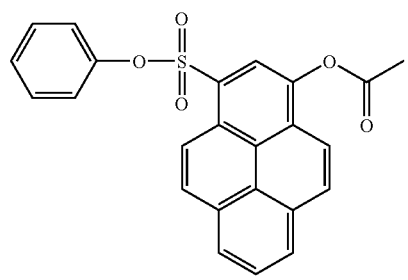

8

Referring to Scheme 12, a 20-mL scintillation vial was charged with 8 (0.15 mmols, 59 mg) and chlorosulfonic acid (2 mL) and stirred at room temperature for 1 h. The dark red solution was dripped into crushed ice and extracted with dichloromethane (3×20 mL). The dichloromethane layer was dried over MgSO$_4$ and concentrated in vacuo to give 9 as an orange-yellow residue (0.08 mmols, 40 mg, 53%).

(Scheme 11)

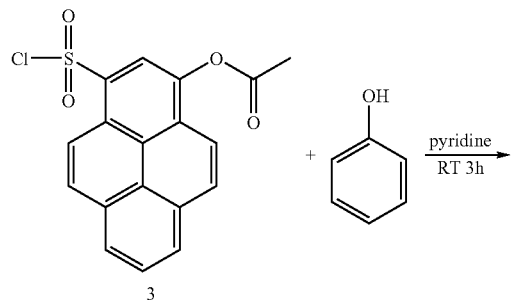

(Scheme 12)

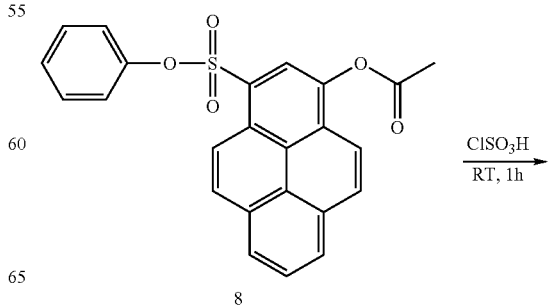

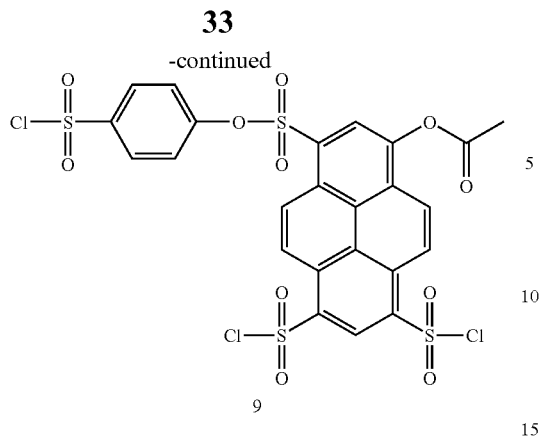
Referring to Scheme 13, a 50-mL round bottom was charged with 9 (0.08 mols, 40 mg), 6 (0.2 mmols, 41 mg), $CH_2Cl_2$ (3 mL) and $NEt_3$ (0.48 mmols, 0.07 mL) and stirred at room temperature for 24.5 h. The red solution was concentrated in vacuo and dissolved in 10% MeOH in $CH_2Cl_2$ and loaded onto Biotage Si 25+M. The product was eluted with MeOH/$CH_2Cl_2$ and isolated to give 18.7 mg of 11, (0.02 mmols, 25%), as a red film.
(Scheme 13)
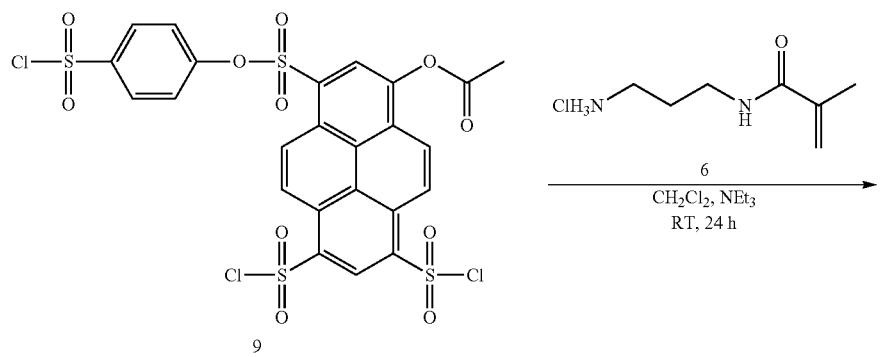
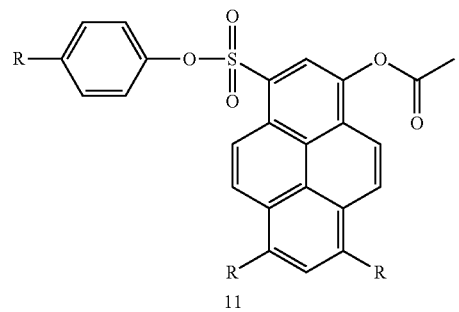
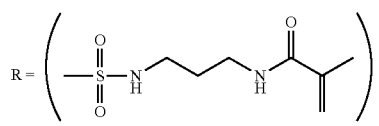

Referring to Scheme 14, a 10-mL round bottom flask equipped with a reflux condenser and an $N_2$ balloon was charged with 11 (0.008 mmols, 8.3 mg) and 5% KOH(aq):MeOH (1.5 mL). The mixture was refluxed at 80° C. for 30 minutes and changed from dark orange to green-yellow. The mixture was cooled to room temperature concentrated in vacuo to give an orange oil. The oil was dissolved in water (2 mL) and loaded onto a Dowex 50W column in the H+ form. The yellow-green solution that passed through was collected along with 3 column volumes and had a pH of about 5. The combined aqueous solution was washed with methylene chloride (3×100 mL) and loaded onto a Dowex 50W column in the Na+ form. The orange-green eluent was lyophilized over 64 h to give 5.9 mg of BisMA as an orange powder.

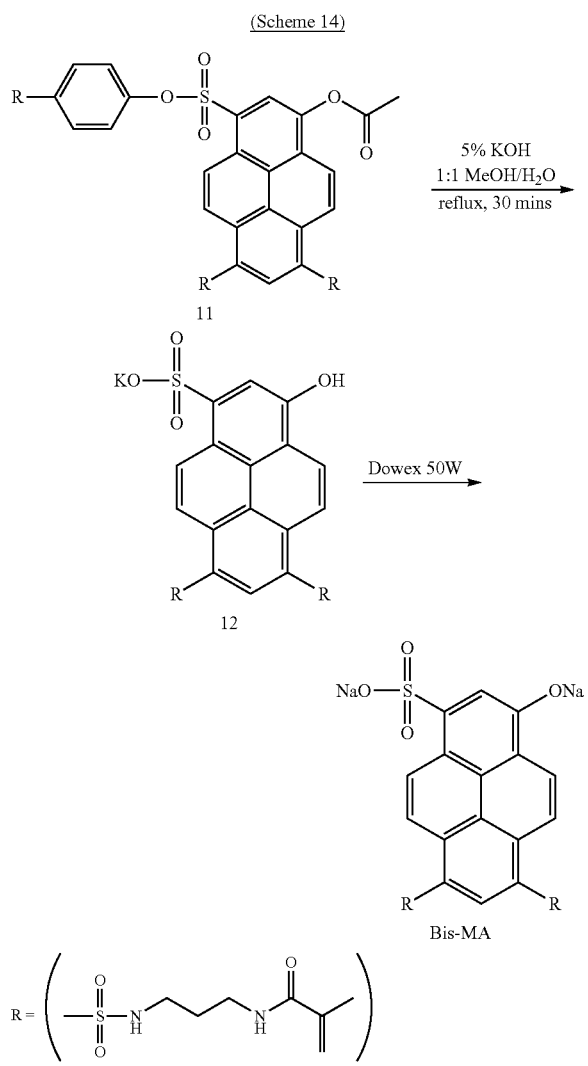

Photophysical Characterization

Figure 9:
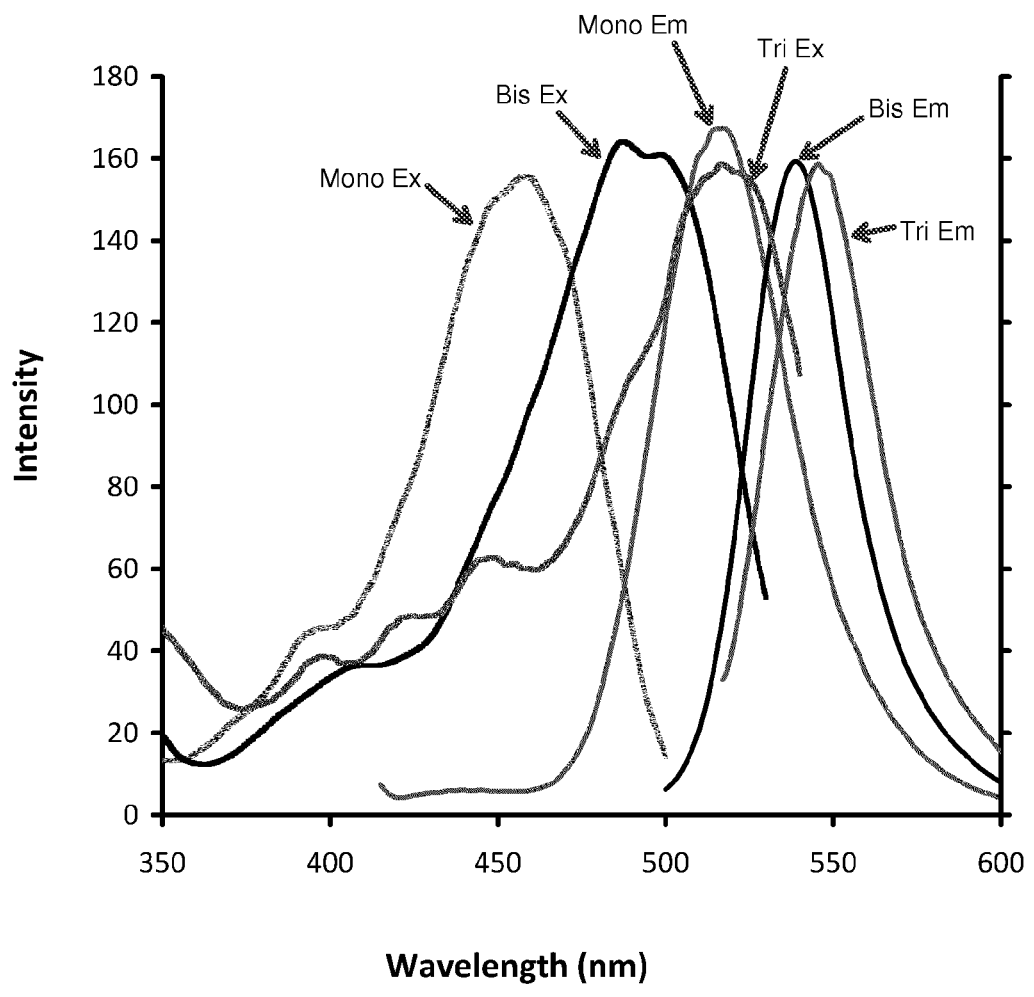
FIG. 9. Comparison of mono, bis and tri-substituted HPTS dyes.

Bis-MA was dissolved in pH 7.4 PBS and its fluorescence was measured on the fluorimeter. FIG. 9 compares Bis-MA with the Mono- and Tri-substituted HPTS derivatives. In line with what was expected, the Bis is red-shifted relative to the Mono product but blue-shifted relative to the Tri product.

Glucose Sensors

Glucose sensors of the present invention comprise a fluorophore operably coupled to a glucose binding moiety, wherein glucose binding causes an apparent optical change in the fluophores concentration (e.g., emission intensity). For example, glucose binding moieties such as viologens appended with boronic acid (e.g., 3,3'-oBBV) or pyridinium salts functionalized with boronic acids are operably coupled to a fluorescent dye such as those described herein. The glucose binding moieties quench the emission intensity of the fluorescent dye, wherein the extent of quenching is reduced upon glucose binding, resulting in an increase in emission intensity related to glucose concentration.

In some embodiments, the glucose sensor systems comprise a means for immobilizing the sensing moieties (e.g., dye-quenchers) such that they remain physically close enough to one another to interact (quenching). Where in vivo sensing is desired, such immobilizing means are preferably insoluble in an aqueous environment (e.g., intravascular), permeable to glucose, and impermeable to the sensing moieties. Typically, the immobilizing means comprises a water-insoluble organic polymer matrix. For example, the dye-quencher may be effectively immobilized with a DMAA (N,N'-dimethylacrylamide) hydrogel matrix, which allows glucose sensing in vivo.

Typical sensor configurations include a light source adapted to generate light at one or more excitation wavelengths, an optical fiber adapted to transmit light from the light source to a chemical indicator system (e.g., a fluorescent dye, quencher and immobilizing polymer), wherein the indicator system is preferably disposed within the light path along a distal region of the optical fiber, which is in contact with a physiological fluid containing an amount of glucose (e.g., within a blood vessel), and a detector adapted to determine the emission fluorescence at one or more emission wavelengths.

Glucose sensor chemistries, device configurations and hardware may include any embodiments disclosed in co-pending U.S. patent application Ser. Nos. 10/456,895, 11/296,898, 11/671,880, 11/782,553, 60/888,477, 60/888,475, 60/917,309, 60/917,307, 60/915,372 and 60/949,145; each of which is incorporated herein in its entirety by reference thereto.

Polymer Matrices for Sensors

For in vivo applications, the sensor is preferably used in a moving stream of physiological fluid, e.g., within a blood vessel, which contains one or more polyhydroxyl organic compounds or is implanted in tissue such as muscle which contains said compounds. Therefore, it is preferred that none of the sensing moieties escape from the sensor assembly. Thus, for use in vivo, the sensing components are part of an organic polymer sensing assembly. Soluble dyes and quenchers can be confined by a semi-permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained.

Preferably the sensing moieties are immobilized in an insoluble polymer matrix, which is freely permeable to glucose. The polymer matrix may be comprised of organic, inorganic or combinations of polymers thereof. The matrix may be composed of biocompatible materials. Alternatively, the matrix is coated with a second biocompatible polymer that is permeable to the analytes of interest.

One function of the polymer matrix is to hold together and immobilize the fluorophore and quencher moieties providing an operable coupling between these moieties, while at the same time allowing contact with the analyte, and binding of the analyte to the boronic acid. To achieve this effect, the matrix is preferably insoluble in the medium, and in close association with it by establishing a high surface area interface between matrix and analyte solution. For example, an ultra-thin film or microporous support matrix may be used. Alternatively, the matrix is swellable in the analyte solution, e.g., a hydrogel matrix is used for aqueous systems. In some instances, the sensing polymers are bonded to a surface such as the surface of a light conduit, or impregnated in a microporous membrane. In all cases, the matrix preferably does not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are preferred for embodiments of this invention. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention may also be monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium chloride, vinyl benzyl trimethyl ammonium chloride, sodium sulfopropyl methacrylate, and the like; crosslinkers include ethylene dimethacrylate, PEGDMA, N,N'-methylene-bis-acrylamide trimethylolpropane triacrylate, and the like. The ratios of monomers are chosen to optimize network properties including permeability, swelling index, and gel strength using principles well-established in the art. The concentration of dye is chosen to optimize emission intensity. The ratio of quencher to dye is adjusted to provide sufficient quenching to produce the desired measurable signal.

Alternatively, a monolithic hydrogel may be formed by a condensation polymerization.

Polymers that are capable of reacting with boronic acids to form boronate esters under the conditions of this method are not preferred as matrix polymers. Such polymers have 1,2- or 1,3-dihydroxy substituents, including but not limited to cellulosic polymers, polysaccharides, polyvinyl alcohol and its copolymers and the like.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. The compound:

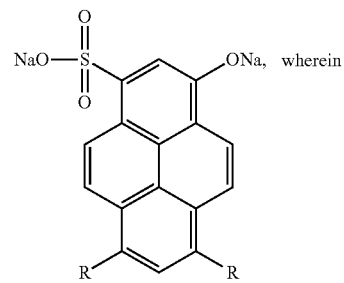

wherein

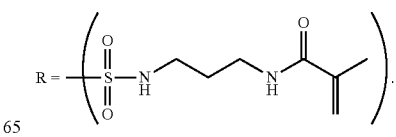

2. A method of making the compound of claim 1 comprising the steps of:
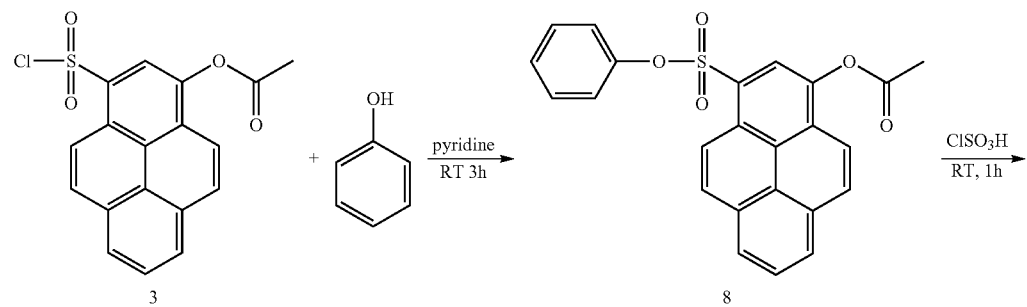
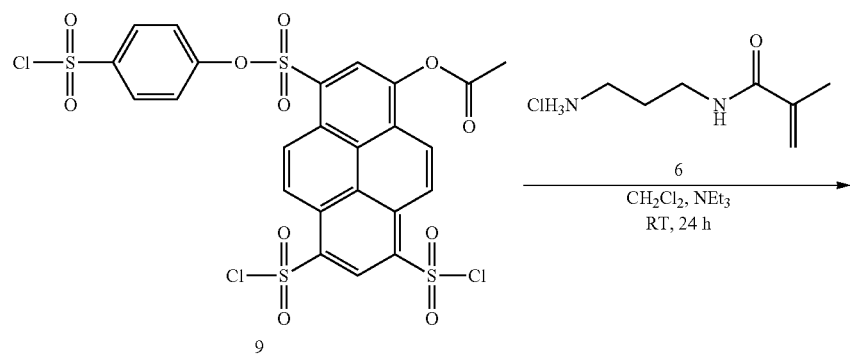
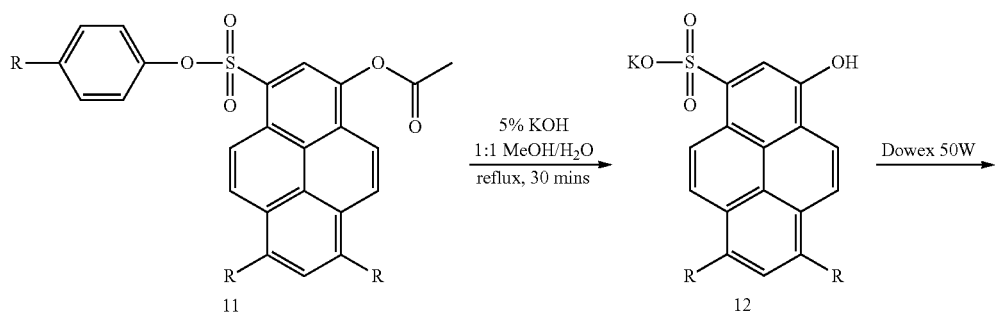

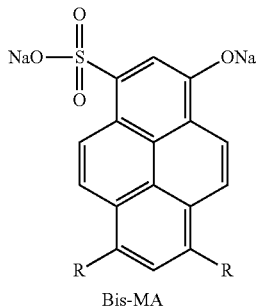

Bis-MA

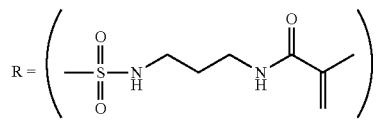

3. A hydrogel comprising a compound of claim 1.

4. A glucose sensor comprising a compound of claim 1.

5. The glucose sensor of claim 4, further comprising a quencher moiety comprising boronic acid.

6. The glucose sensor of claim 5, wherein said quencher moiety comprising boronic acid is 3,3'-oBBV:

7. A glucose sensor comprising a hydrogel of claim 3.

8. A glucose sensor of claim 7 wherein the hydrogel further comprises a quencher moiety comprising boronic acid.

9. A glucose sensor of claim 8, wherein said quencher moiety comprising boronic acid is 3,3'-oBBV.

* * * * *